(12) United States Patent
Carlson

(10) Patent No.: US 10,586,744 B2
(45) Date of Patent: Mar. 10, 2020

(54) METHOD FOR OPTIMIZING DRY ABSORBER EFFICIENCY AND LIFETIME IN EPITAXIAL APPLICATIONS

(71) Applicant: Applied Materials, Inc., Santa Clara, CA (US)

(72) Inventor: David K. Carlson, San Jose, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 25 days.

(21) Appl. No.: 15/934,679

(22) Filed: Mar. 23, 2018

(65) Prior Publication Data

US 2018/0277455 A1     Sep. 27, 2018

Related U.S. Application Data

(60) Provisional application No. 62/476,357, filed on Mar. 24, 2017.

(51) Int. Cl.

| | |
|---|---|
| *B01D 53/04* | (2006.01) |
| *H01L 21/66* | (2006.01) |
| *C23C 16/44* | (2006.01) |
| *H01L 21/02* | (2006.01) |
| *H01L 21/67* | (2006.01) |
| *G01N 21/3504* | (2014.01) |
| *G01N 30/02* | (2006.01) |
| *G01J 3/42* | (2006.01) |
| *G01N 21/35* | (2014.01) |

(Continued)

(52) U.S. Cl.
CPC .......... *H01L 22/26* (2013.01); *B01D 53/0454* (2013.01); *C23C 16/4405* (2013.01); *C23C 16/4412* (2013.01); *H01L 21/0262* (2013.01); *H01L 21/67253* (2013.01); *G01J 3/42* (2013.01); *G01N 21/3504* (2013.01); *G01N 21/783* (2013.01); *G01N 2021/3595* (2013.01); *G01N 2021/8416* (2013.01); *G01N 2030/025* (2013.01)

(58) Field of Classification Search
CPC .... C23C 16/4405; C23C 16/4412; G01J 3/42; G01N 21/3504; G01N 21/783; G01N 2021/3595; G01N 2021/8416; G01N 2030/025; H01L 21/0262; H01L 21/67253; H01L 22/26; B01D 53/0454
USPC .......................................................... 96/111
See application file for complete search history.

(56) References Cited

U.S. PATENT DOCUMENTS

| | | | | |
|---|---|---|---|---|
| 5,856,198 A | * | 1/1999 | Joffe ................... | B01D 53/0454 422/82.01 |
| 6,617,175 B1 | * | 9/2003 | Arno ..................... | G01J 5/0014 438/7 |

(Continued)

*Primary Examiner* — Frank M Lawrence, Jr.
(74) *Attorney, Agent, or Firm* — Patterson + Sheridan LLP

(57) ABSTRACT

Increasing efficiency of absorbers is provided herein. In some embodiments, a method of processing a substrate may include determining a quantity of a removal species in an effluent stream flowing from a semiconductor processing chamber, wherein determining comprises: detecting or predicting a quantity of the removal species upstream of a chamber abatement apparatus in the effluent stream flowing from the semiconductor processing chamber; and removing the removal species from the effluent stream with the chamber abatement apparatus if the determined quantity of the removal species exceeds a threshold value of the removal species.

9 Claims, 7 Drawing Sheets

(51) Int. Cl.
    *G01N 21/84*          (2006.01)
    *G01N 21/78*          (2006.01)

(56) References Cited

U.S. PATENT DOCUMENTS

| | | |
|---|---|---|
| 7,252,858 B2 | 8/2007 | Carlsen |
| 2002/0092421 A1* | 7/2002 | Hayes .................... B01D 53/40 <br> 95/107 |
| 2013/0139690 A1* | 6/2013 | Ohuchi .................. B01D 53/02 <br> 96/4 |

* cited by examiner

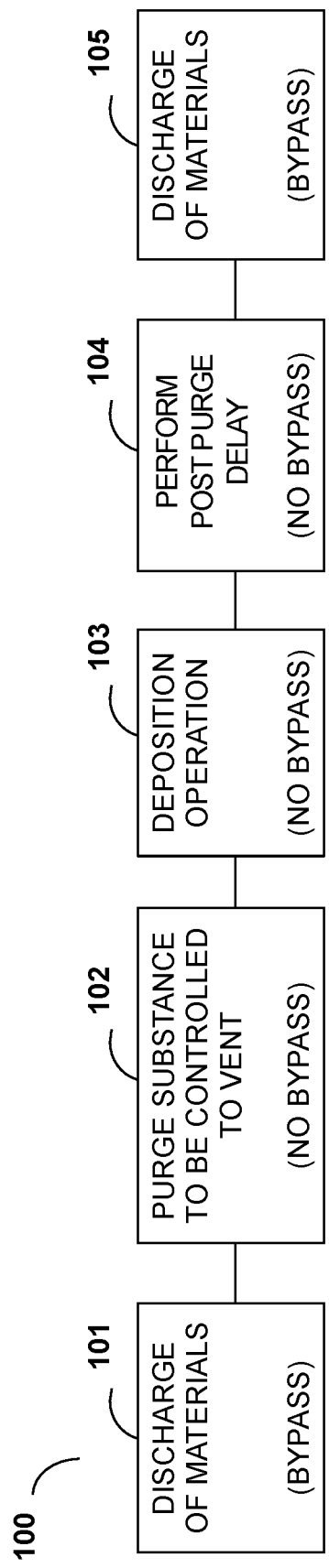
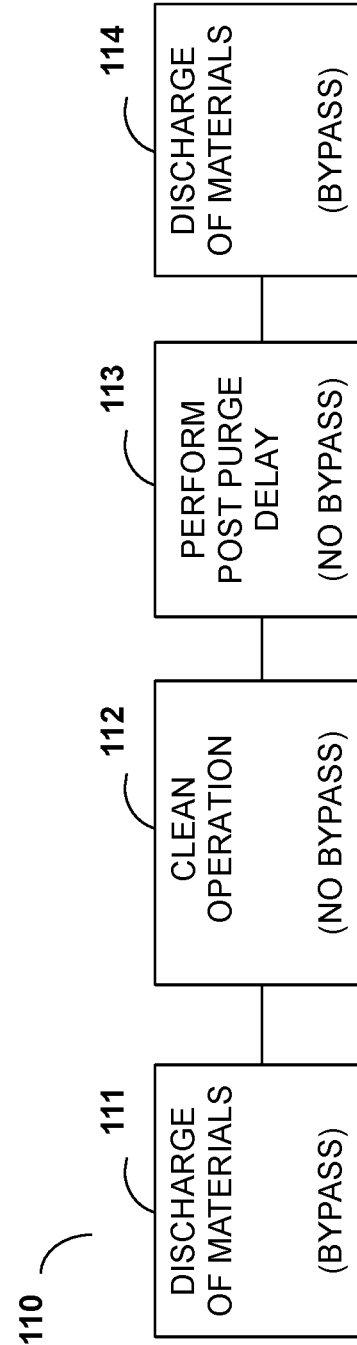
FIG. 1A
FIG. 1B

METHOD FOR OPTIMIZING DRY ABSORBER EFFICIENCY AND LIFETIME IN EPITAXIAL APPLICATIONS

CROSS REFERENCE TO RELATED APPLICATIONS

This application claims benefit of U.S. Provisional Patent Application No. 62/476,357, filed Mar. 24, 2017, the entirety of which is herein incorporated by reference.

FIELD

Embodiments of the present invention generally relate to semiconductor processing equipment.

BACKGROUND

Process chambers used to deposit film layers using chemical vapor and other deposition techniques can exhaust therefrom materials which must be removed from the exhaust stream to meet environmental and safety regulations. Typically, the exhaust stream is incinerated in a burn box, and in some cases, wet scrubbed, to remove these materials. However, certain compositions or elements cannot be abated by incineration or wet scrubbing. To remove these materials, chemical absorbers are placed in the exhaust stream prior to additional abatement apparatus, to remove some particulates and/or gases from the exhaust stream in point of use applications, where, for example, the exhaust stream is incinerated in a burn box, and optionally wet scrubbed, after passing through the absorber and before entering the house exhaust system. For example, during deposition of group III-V compounds, arsenic and phosphorus are used as a dopant material. These materials cannot be removed from the exhaust stream using incineration or wet scrubbing techniques, and thus an absorber is located in the exhaust piping of the deposition chamber upstream of the burn box and where used, the wet scrubber. The use of compounds such as arsenic-based and phosphorus-based compounds requires use of absorbers in the exhaust path to capture these materials.

The deposition chamber in which the doped III-V thin film is being deposited must be periodically cleaned, using an acidic gas such as HCl. During the cleaning, the HCl is broken down in a plasma and the chlorine is used to remove III-V material which has deposited on the walls of the chamber and the internal chamber components. The etched material is likewise exhausted into the same abatement system used during deposition. Chlorine in the exhaust stream is absorbed in the absorber, significantly reducing the useful life of the absorbing material therein. When the absorber's ability to absorb material declines, the deposition tool has to be shut down, and the absorber material therein replaced, resulting in lost productivity from the deposition tool.

For most substrate processing applications, there is a significant cost associated with both the deposition materials and the exhaust abatement and disposal. The cost of dry absorbers is a big driver in the cost-per-wafer pass for some processes performed in traditional semiconductor fabs. The load of particulates and absorbable gases on dry absorbers increases downtime for cycling the absorbers, and therefore increased cost in the operation of a fab.

Therefore, there is a need for systems and processes that provide for a longer lifetime of the dry absorber.

SUMMARY

Methods for optimizing dry absorber efficiency and lifetime are provided herein. In some embodiments, a method is provided that includes determining a quantity of a removal species in an effluent stream flowing from a semiconductor processing chamber, wherein determining comprises: detecting or predicting a quantity of the removal species upstream of a chamber abatement apparatus in the effluent stream flowing from the semiconductor processing chamber; and removing the removal species from the effluent stream with the chamber abatement apparatus if the determined quantity of the removal species exceeds a threshold value of the removal species.

In other embodiments, a method is provided that includes performing an epitaxial process in a semiconductor processing chamber; concurrently predicting or detecting, upstream of a chamber abatement apparatus, a quantity of a removal species in an effluent stream flowing from a semiconductor processing chamber, the chamber abatement apparatus comprising a bypass; and removing the removal species from the effluent stream with the chamber abatement apparatus if the quantity of the removal species exceeds a threshold value of the removal species.

In some embodiments, a computer system is provided that is programmed to perform a method that includes the operations of determining a quantity of a removal species in an effluent stream flowing from a substrate processing chamber; and selecting a chamber abatement apparatus to remove the removal species, wherein selecting is based on the quantity of the removal species reaching a threshold value.

In some embodiments, a non-transitory computer readable medium is provided that includes instructions that cause a computer system to control a substrate processing apparatus to perform a process, comprising: determining a quantity of a removal species in an effluent stream flowing from a substrate processing chamber; comparing the determined quantity of the removal species to a first quantity of the removal species and to a second quantity of the removal species; actuating one or more control valves to direct the effluent stream to one or more dry absorbers if the determined quantity of the removal species is greater than the first quantity; and actuating the one or more control valves to direct the effluent to bypass the one or more dry absorbers if the determined quantity of the removal species is less than the second quantity.

Other and further embodiments are described below.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

FIG. 1A is a flow chart depicting a deposition process in accordance with some embodiments.

FIG. 1B is a flow chart depicting a cleaning process in accordance with some embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 2:
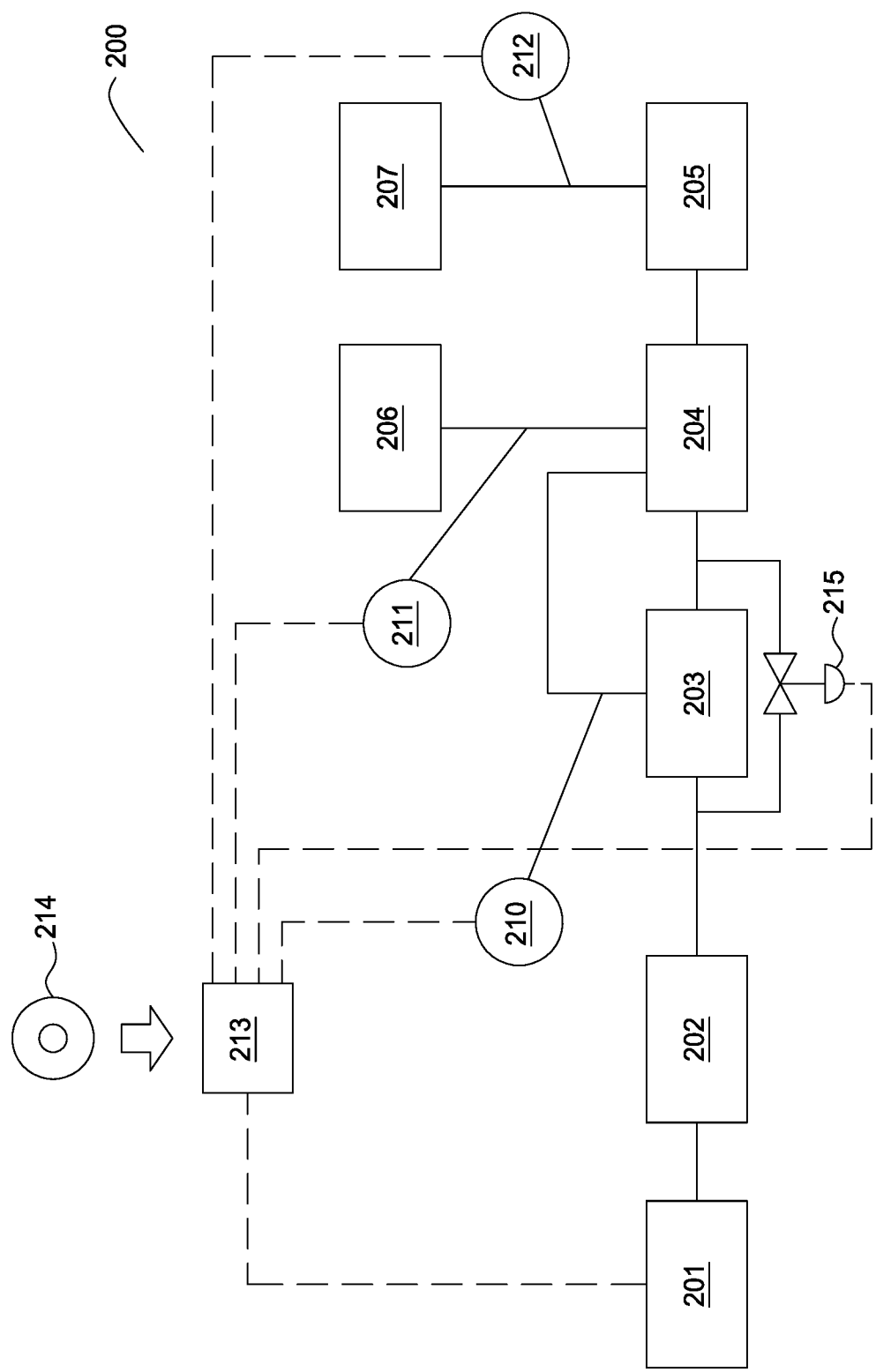
FIG. 2 is a block configuration depicting a semiconductor fab in accordance with some embodiments.

The methods and materials described herein provide cost efficient usage of dry absorbers as compared to conventional operating methods. Conventional semiconductor fabs typically have a house exhaust system that is primarily designed for nonreactive waste gases, and an abatement apparatus, which is dedicated to the house exhaust system, that is designed for reactive gases and/or particulates. The abatement apparatus can have absorbers, and such absorbers are typically used prior to abatement in order to remove some particulates and/or gases from industrial exhaust streams. In conventional semiconductor fabs, all of the gas and/or particulates that are not consumed during semiconductor manufacturing processes flows through the chamber abatement apparatus (which can include absorbers). In the present disclosure, the chamber abatement apparatus for an epitaxial system can be controlled to select use thereof only when use thereof will help reactor effluent stay within set effluent discharge boundaries. The specific processes run can be characterized for the discharge therefrom, and the process recipe can send a command to select use of the absorber. Using the programming of the control system in order to predict at what points the absorber is to be used increases the lifetime of the dry absorber on a per wafer pass through the chamber to which it is connected basis.

For purposes of this disclosure, the "chamber abatement apparatus" is dedicated to the tool or substrate processing chamber and is not dedicated to the house exhaust system. That is, the chamber abatement apparatus is local to the tool or substrate processing chamber. The chamber abatement apparatus includes a bypass, which allows bypass of an absorber. The chamber abatement apparatus includes an absorber.

For purposes of this disclosure, and unless otherwise specified, a "removal species" refers to a substance to be controlled, as specified by a manufacturing facility, and is characterized as having a threshold quantity (i.e., in ppm) at which that species can no longer remain in the manufacturing facility exhaust system. Removal species includes arsenic containing materials, phosphorus containing materials, cyanide containing materials, and phosgene.

For purposes of this disclosure, and unless otherwise specified, the terms "removal species" and "substance to be controlled" may be used interchangeably.

For purposes of this disclosure, and unless otherwise specified, the term "quantity" refers to an amount or concentration.

For purposes of this disclosure, and unless otherwise specified, a "time delay" refers to an amount of time between the introduction of a gas comprising a removal species into a substrate processing chamber and when one can expect the exhaust gas to have that removal species in it at a quantity at which the gas must be abated. During the time delay, the dry absorber can be bypassed if the quantity of the removal species is below a threshold value. For example, the time delay is the amount of time between introduction of arsenic containing materials into the chamber and when the arsenic containing materials are observed at the chamber abatement apparatus at a quantity at which the arsenic containing materials must be abated.

The time delay is based on various factors including:

1) a volumetric flow rate, Q ($m^3$/sec), of a gas comprising the removal species flowing from the substrate processing chamber.

2) a quantity of the removal species in a gas being introduced into the substrate processing chamber.

3) a quantity of the removal species which reacts with (and/or etches) a wafer, chamber wall, and/or other component inside the substrate processing chamber. This indicates the amount of the removal species that is in the effluent stream flowing from the substrate processing chamber.

4) a cross-sectional area of an effluent stream pipe/tube that connects the substrate processing chamber and the chamber abatement apparatus.

5) a length of the effluent stream pipe/tube between the substrate processing chamber and the chamber abatement apparatus.

For purposes of this disclosure, and unless otherwise specified, the terms "time delay," "wait time," and "lag time" may be used interchangeably.

The methods described herein can be used to determine, detect, and predict the quantity of a removal species in the effluent flowing from a substrate processing chamber. As an example, a quantity of a removal species, such as an arsine compound, in the effluent stream may be determined based on the quantity of the arsine material, or a related material, being deposited on the substrate.

Although the present disclosure is illustrated in the context of epitaxial applications, one of ordinary skill in the art will recognize that the present disclosure is not limited to epitaxial applications. On the contrary, the bypass method and substrate processing chamber described herein may be used in connection with any type of semiconductor manufacturing process.

The chamber abatement apparatus can be used with any substrate processing chamber and can be used for any process that is performed in the substrate processing chamber including deposition processes, chamber clean processes, and substrate etch processes. In each of these processes, a removal species can be used. When the quantity of the removal species in an effluent stream flowing from the substrate processing chamber is below a threshold quantity of removal species, the chamber abatement apparatus is placed in a bypass mode (that is, the effluent stream bypasses the absorber), and is operated to direct the flow of the effluent stream to a house exhaust system. When the quantity of removal species in an effluent stream flowing from the substrate processing chamber is at or above a threshold quantity of the removal species, the chamber abatement apparatus is placed in a no-bypass mode (that is, the effluent stream does not bypass the absorber), and is operated to direct the flow of the effluent stream to the absorber.

Methods for optimizing dry absorber efficiency and lifetime are described herein. During deposition, etch and substrate processing chamber cleaning processes, a reactive species is introduced into the chamber, often in combination with a carrier species such as Nitrogen or Argon. Where the reaction products of the deposition, etch or cleaning process are toxic, pyrophoric, or corrosive, or the discharge thereof into the environment is regulated, the exhaust stream from the substrate processing chamber must be abated, which is most commonly done using an abatement system dedicated to the substrate processing chamber, or to a plurality of substrate processing chambers located near one another, before the treated exhaust from the substrate processing chamber is exhausted to what is commonly called the "house" exhaust. Once the process of substrate layer etching, substrate layer depositing or substrate processing chamber cleaning is completed, the supply of the reactive gas species to the substrate processing stops, and a purge gas, such as nitrogen or argon, is flowed into the substrate processing to flush away any remaining process or cleaning gases, and any products of reaction in the substrate processing chamber, into the chamber exhaust. In some processes, the film to be formed, or selectively etched, includes species of compounds which must be abated, and can only be abated by absorption thereof into an absorber material, which is commonly located in an absorber located in the exhaust piping or tubing between the chamber exhaust port and any other abatement required for the process. For example, where III-V compounds are being deposited in a chamber, gaseous dopants such as arsenic and phosphorous compounds are also introduced into the chamber to be incorporated into the film layer being deposited on the chamber walls. These compounds must be removed from the exhaust stream, and cannot be abated by incineration thereof in a burn box in the abatement system used to abate the gaseous materials used to form the main III-V composed layer. Thus, in this instance, an absorber has been used between the chamber exhaust port and the remaining abatement system, such as a burn box and optionally a wet scrubber. Herein, the dry absorber material, and thus the flow of the exhaust through the absorber in which they are held, is be controlled to cause the use thereof only when the use thereof is required to maintain the process chamber exhaust effluent within set effluent discharge limits, for example, below upper limits of certain gases measured in milliliters per cubic meter which can be exhausted to the house exhaust. The specific processes run in the process chamber can be characterized for their resultant effluent discharge, and the process recipe can be configured to cause the system controller to send a command to activate use of the absorber, such as by controlling a valve in the chamber exhaust flow line connected to the chamber exhaust port to close off a bypass line directing the exhaust flow around the absorber so it flows directly into the burn box, and opening a flow line to the absorber to flow the exhaust through the absorber and thence to the burn box. Using the programming of the system controller in order to predict at what points the absorber is to be used increases the lifetime of the dry absorber on a per wafer pass through the chamber to which it is connected basis. As an example, a quantity of a removal species, such as an arsine or phosphorous compound in the effluent stream, may be determined based on the quantity of the substance, or a related substance, being deposited on the substrate in comparison with the amount of the substance being introduced into the deposition chamber. A time delay may be defined based on how much material is deposited, and during that time delay, the dry absorber can be bypassed if the quantity of the removal species is below a threshold value.

As an example of the operation of the chamber abatement apparatus, and according to an embodiment, a deposition process is performed, and the exhaust stream thereof is abated. FIG. 1A is a flow chart setting forth a method 100 of selecting the flow path of the chamber exhaust. A bypass mode, to bypass the absorber, may be selected by a computer program or an operator when the quantity of a removal species in the chamber exhaust is below a threshold value. As an example of an embodiment, the deposition process includes flowing inert, nonreactive, and/or non-abatement process gases such as $N_2$ into the chamber, and discharging them through the exhaust as a discharge at operation 101 during which the chamber abatement apparatus is placed in bypass mode and the discharge flows to the semiconductor fab exhaust without flowing through the absorber. The process gases remaining from a prior substrate process operation in the substrate processing chamber are purged at operation 102, so as to remove these gases before the substrate process chamber valve is opened and the substrate removed therefrom. Because a removal species may be present at operation 102, the chamber abatement apparatus will switch out of a bypass mode and enter into a no-bypass mode so that the effluent stream will flow through the absorber before flowing into the burn box. No-bypass mode of the absorber will also occur during a deposition operation at operation 103 and during a post-purge delay at operation 104 if a removal species is used during the deposition operation 103 and/or the post-purge delay operation 104. The post-purge delay of operation 104 is a lag time subsequent to the end of the deposition operation where a material of the precursor was deposited on a substrate. Once the amount of time for the post-purge delay has passed, the quantity of the removal species in the effluent stream will predictably be below a threshold value at which the material must be abated by absorption, and the chamber abatement apparatus is placed back into bypass mode to bypass the absorber, at operation 105. Alternately, a detector can be used to detect the quantity of the removal species and the chamber abatement apparatus can be placed back into bypass mode. Method 100 may be performed by a computer program or operator.

The operation of the chamber abatement apparatus during a chamber clean process and a substrate etch process is used similarly as described above for the deposition process.

In some embodiments, a chamber clean process to remove materials deposited on the surfaces of the substrate processing chamber is performed. Where the chamber has been used to deposit a material which includes a material which must be abated by absorption, that material will be present on the chamber surfaces and will be freed therefrom, and flowed into the chamber exhaust, during the cleaning operation. However, it has been found that the quantity of these materials in the exhaust from the chamber cleaning process declines rapidly after about the first 30 seconds of the chamber clean process, to a value below which they must be abated. Additionally, the cleaning gas which can be abated by combustion in the burn box and/or, wet scrubbing, if passed through the absorber, will be absorbed, reducing the capacity of the absorber material to remove removal species which can only be abated by absorption. As shown in FIG. 1B, in a method 110 of a chamber clean process, the bypass mode may be selected by a computer program or an operator when the quantity of removal species in the chamber exhaust falls below a threshold value. As an example of an embodiment, the clean process includes discharge 111 from the substrate processing chamber of gases such as $Cl_2$ and $H_2$, Cl compounds, deposition material etched from the substrate processing chamber surfaces which includes the removal species therein (for example As or P in atomic or another compound form) and the chamber abatement apparatus is initially placed in the non-bypass mode. When the concentration of the removal species in the chamber exhaust stream which can only be abated by absorption falls below the threshold at which they must be abated from the exhaust stream, the abatement system is in placed in the absorber bypass mode.

During etching of a chamber wall or internal chamber components (at operation 112), if the chamber wall being etched, or the etchant, includes a removal species, the absorber is not bypassed during the etching process, and also after etching of the chamber wall is completed where the absorbed species or compound may still be in the exhaust stream flowing from the chamber. During this cleaning operation, an acidic gas such as HCl may be used and is broken down in a plasma, and the chlorine is used to remove material which has deposited on the walls of the chamber and the internal chamber components during a substrate deposition process. The length of this post purge delay 113 after etching is completed is based on a prediction of when the abated species in the exhaust stream will fall below the threshold limit at which it must be abated. The post purge delay 113 is a time delay as discussed above. Once the amount of time for the post-purge delay has passed, the quantity of removal species in the effluent stream will predictably be, or measured as, below a threshold value, and the abatement system can then be placed back into bypass mode, at operation 114. This method may be performed by a computer program or an operator.

This method 110 of a chamber clean process provides the ability to predict when the amount of arsenic (As) containing materials or phosphorous (P) containing materials in the chamber cleaning effluent is below a threshold value at which it must be abated. When the amount of As- or P-containing materials is below the threshold value, the absorber can be bypassed. Because the absorber is bypassed, the absorber receives a lower quantity of chlorine containing materials that are exhausted during a chamber clean process. In turn, the number of substrates that can be processed in the substrate processing chamber is increased before the absorbent material in the absorber must be replaced.

FIG. 2 shows a block configuration of a semiconductor fab according to an embodiment. Gases are flowed into a substrate processing chamber 201. The gases not consumed in the substrate processing chamber are vented from the substrate processing chamber 201 through an exhaust connected to a vacuum pump 202. The vacuum pump 202 pumps the gas through an absorber 203 (which may be a dry absorber) then to a conventional burn box which is a flammable abatement system 204, and then to a conventional wet scrubber which is a waste water stream system 205. The flammable abatement system 204 and the waste water stream system 205 are used to remove and neutralize exhaust gases, removal species, particulates, process wastes, and by-products of the process performed in the substrate processing chamber. The gases flowing from the flammable abatement system 204 are vented to a burn box exhaust 206, and the water stream flowing from the scrubber 205 flows to a drain 207. In addition to the vacuum pump 202 on the chamber exhaust that pumps the exhaust gas stream through the dry absorber, the house exhaust may be used to pull the gas through the dry absorber.

Locations 210, 211, and 212 represent detection points where an effluent stream can be tested for a quantity of material to be abated. According to some embodiments, the material may be a removal species. In some embodiments, the measurements gathered from detection points 210, 211, and 212 may be used to create a time delay after the end of a process, or process step, in the deposition chamber after which the concentration of species and compounds in the chamber effluent or exhaust stream which must be abated by absorption fall below the threshold limit at which abatement is no longer required.

Detection point 210 is located between the dry absorber 203 and the flammable abatement system 204. Detection point 211 is located between the flammable abatement system 204 and the flammable abatement system exhaust 206. Detection point 212 is located between the water stream coming from waste water stream system 205 and the drain 207.

Sampling at detection points 210, 211, and 212 may be used to repeatedly measure a quantity of a removal species in the effluent stream, whether or not the chamber abatement apparatus is in bypass mode. When the quantity of a removal species is determined to be above a threshold value at which it must be abated, a controller (which may be a user or a computer system, as described below) in a control system actuates one or more control valves to direct the effluent to pass through the dry absorber. When the quantity of a removal species is determined to be below a threshold value at which point it no longer needs to be abated from the exhaust stream, the controller of the control system actuates one or more control valves to direct the effluent to bypass the dry absorber. As a result, where the exhaust stream contains additional gas species or compounds which will be absorbed by the absorber, but these species and compounds can be abated by incineration, wet scrubbing, or both, the quantity or load of these species and compounds abatable by other mechanisms deposited or absorbed by the absorber is significantly reduced, and the number of substrates or wafers which can be processed through the process chamber before the absorbent, i.e., absorbing material, in the absorber must be replaced, is significantly increased.

As shown in FIG. 2, a computer system 213 performs the instructions provided in a non-transitory computer readable medium 214. The non-transitory computer readable medium can contain instructions to perform the methods described herein. Alternately, the instructions to perform the methods described herein may be added to the non-transitory computer readable medium. The computer system is connected to control valve 215, substrate processing chamber 201, and to sampling points 210, 211, and 212. According to some embodiments, the computer system can select a control valve 215 that directs the flow of the effluent (with or without removal species) to the burn box 204. This can be accomplished by sending a signal to a control valve to change the flow path of the chamber exhaust such that the effluent stream of the chamber exhaust flows through the absorber 203 (or when the removal species is below a threshold level, bypasses the absorber 203 and flows directly into the flammable abatement system).

According to an embodiment, the absorber can be maintained in a bypass mode when no removal species will be introduced to the substrate processing chamber 201. A software interlock (either controlled by a user or a computer) may be used such that when any removal species is introduced into the substrate processing chamber 201, the absorber may be immediately scheduled to be switched from bypass mode after the time delay, which may be a time delay of zero. The time delay may be adjusted or set based on various parameters, as described above.

As described below, a redundant software recipe control may be implemented when removal species are to be introduced into the substrate processing chamber or into the chamber exhaust, to allow extended delay times based both the results of chemical analysis of the quantity or concentration of the removal species in the post flammable abatement system 204 exhaust discharge into the house exhaust and in the wet scrubber water discharge. Chemical analysis may be performed by optical absorption methods. Chemical analysis may be performed by methods known to those skilled in the art including gas chromatography (GC), Fourier transform infrared spectroscopy (FTIR), solid state gas detection, electrochemical gas detection, and color change of a reactive media (such as use of Dräger short term tubes).

Figure 3A:
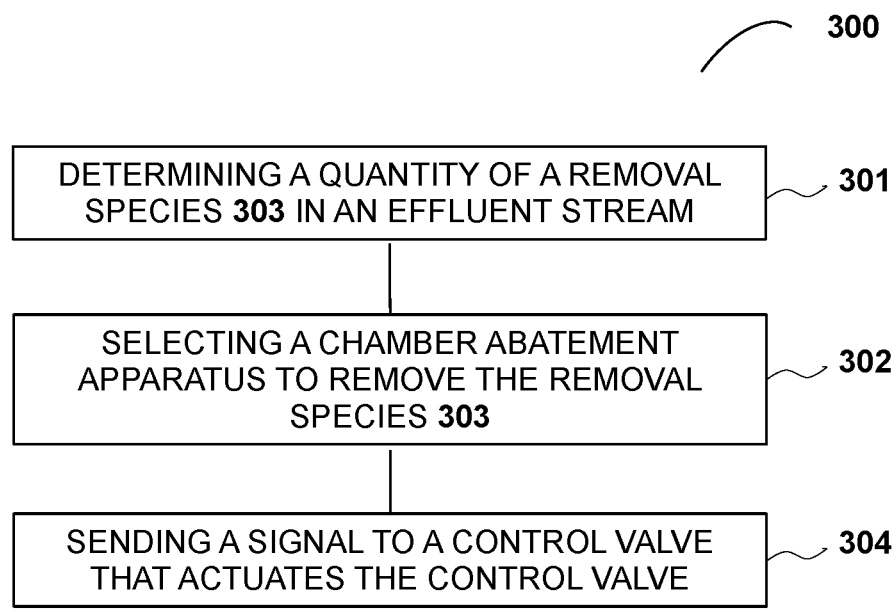
FIG. 3A depicts a computer system programmed to perform a method in accordance with some embodiments.

Referring to FIG. 3A, an embodiment of a computer system programmed to perform a method of selecting a chamber abatement apparatus is provided. The method 300 includes determining a quantity of removal species 303 in an effluent stream of a chamber exhaust flowing from a semiconductor processing chamber, at operation 301; and selecting a chamber abatement apparatus to remove the removal species if the effluent stream requires abatement, at operation 302, wherein selecting is based on the quantity of the removal species in the effluent stream of a chamber exhaust flowing from the substrate processing chamber reaching a threshold value of the removal species. Alternatively, or in addition to, selecting may be based on the time delay when the absorber can be bypassed if the quantity of the removal species in the effluent stream of a chamber exhaust flowing from the substrate processing chamber is below a threshold value of the removal species. Selecting the chamber abatement apparatus may include operating a switch, or a control valve, to direct the flow of the effluent stream of the chamber exhaust to the chamber abatement apparatus for the effluent. This can be accomplished by a controller sending a signal to a control valve to change the flow path of the exhaust stream such that the effluent in the exhaust stream flows through the absorber (or when the removal species is below a threshold level, bypasses the absorber), at operation 304. Selecting the chamber abatement apparatus may also be accomplished by a controller sending a signal to a control valve which actuates the control valve. Actuating may be accomplished by a pneumatic or fluid circuit. The control valve then directs the flow of the effluent stream in the exhaust stream to the selected chamber abatement apparatus. In some embodiments, the method includes forming a doped epitaxial layer on a substrate in the process chamber, such as a doped III-V layer.

Figure 3B:
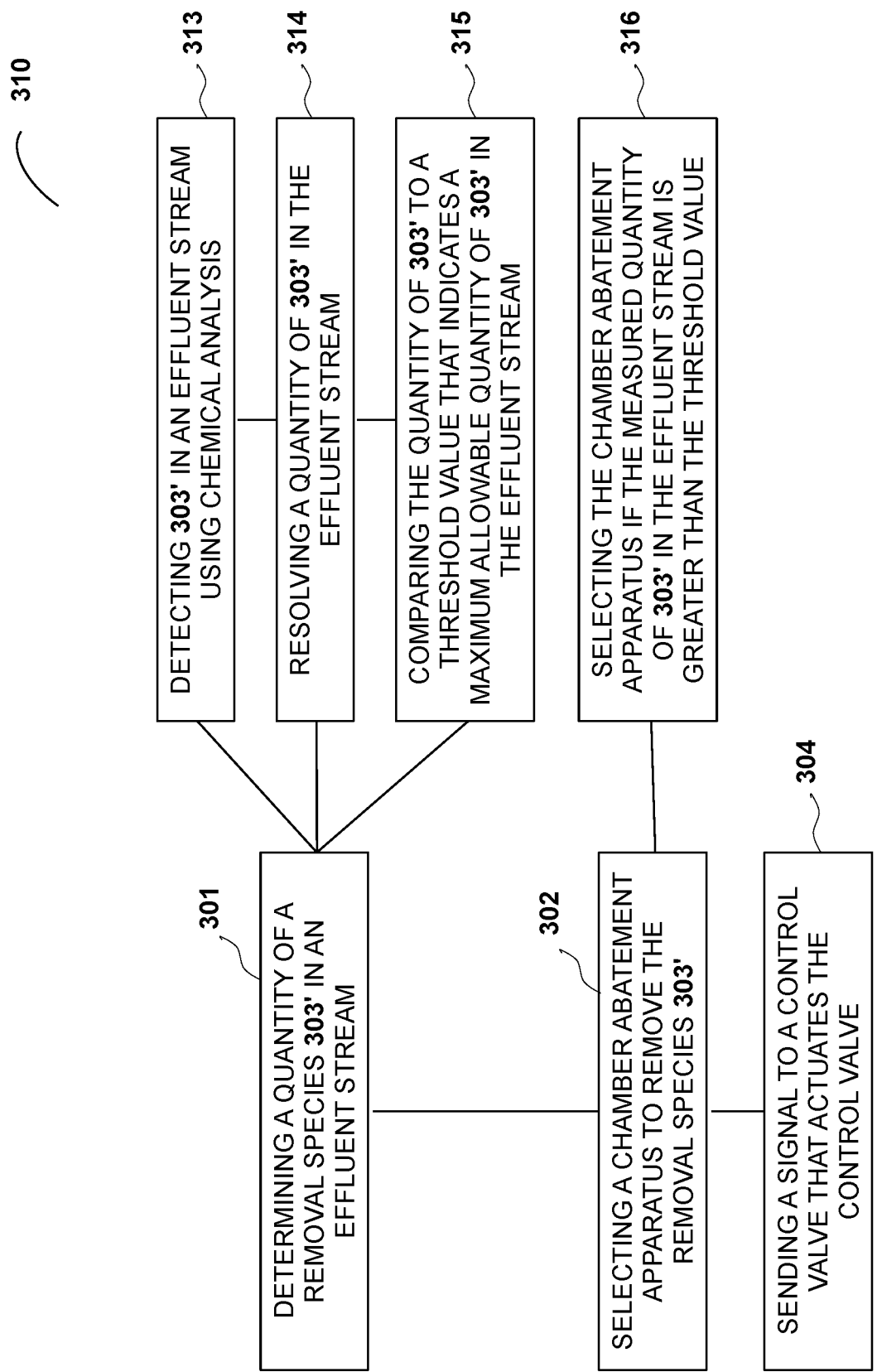
FIG. 3B depicts a computer system programmed to perform a method in accordance with some embodiments.

Referring to FIG. 3B, an embodiment of a computer system programmed to perform a method of selecting a chamber abatement apparatus is provided. The method 310 includes determining a quantity of the removal species 303' in an effluent stream of a chamber exhaust flowing from a semiconductor processing chamber, at operation 301; and selecting a chamber abatement apparatus to remove the removal species if the species requires abatement, at operation 302, wherein selecting is based on the quantity of the removal species in the effluent stream of a chamber exhaust flowing from the substrate processing chamber compared to a threshold value of the removal species in the exhaust stream from the substrate processing chamber. Alternatively, or in addition to, selecting is based on the time delay when the absorber can be bypassed if the quantity of the removal species in the effluent stream of a chamber exhaust flowing from the substrate processing chamber is below a threshold value of the removal species. Determining a quantity of the removal species 303' in the effluent stream of a chamber exhaust flowing from the substrate processing chamber further includes detecting a species in the effluent stream using chemical analysis, at operation 313. Chemical analysis may be performed by optical absorption methods. Chemical analysis may be performed by methods known to those skilled in the art including gas chromatography (GC), Fourier transform infrared spectroscopy (FTIR), solid state gas detection, electrochemical gas detection, and color change of a reactive media (such as use of Dräger short term tubes). Chemical analysis allows the quantity of the removal species 303' in the effluent stream of the chamber exhaust flowing from the substrate processing chamber to be resolved, at operation 314. At operation 315, the quantity of the removal species 303' is compared to a threshold value which indicates a maximum allowable quantity of the removal species in the effluent stream of the chamber exhaust which may permissibly be flowed into the house exhaust.

At operation 316, the chamber abatement apparatus is selected (i.e., by switching off the bypass valve) if the measured quantity of the removal species in the effluent stream of a chamber exhaust flowing from the substrate processing chamber is greater than the threshold value of the removal species. Selecting the chamber abatement apparatus may include operating a control valve that directs the flow of the effluent stream to the chamber abatement apparatus. This can be accomplished by a controller sending a signal to a control valve to change the flow path of the effluent stream of the chamber exhaust such that the effluent flows through the absorber (or when the removal species is below a threshold level, bypasses the absorber), at operation 304. Selecting the chamber abatement apparatus may also be accomplished by a controller sending a signal to a control valve which actuates the control valve. Actuating may be accomplished by a pneumatic or fluid circuit. The control valve then changes the exhaust flow path to direct the flow of the effluent stream to the selected chamber abatement apparatus. In some embodiments, the method includes forming an epitaxial layer on a substrate in the substrate processing chamber.

Figure 3C:
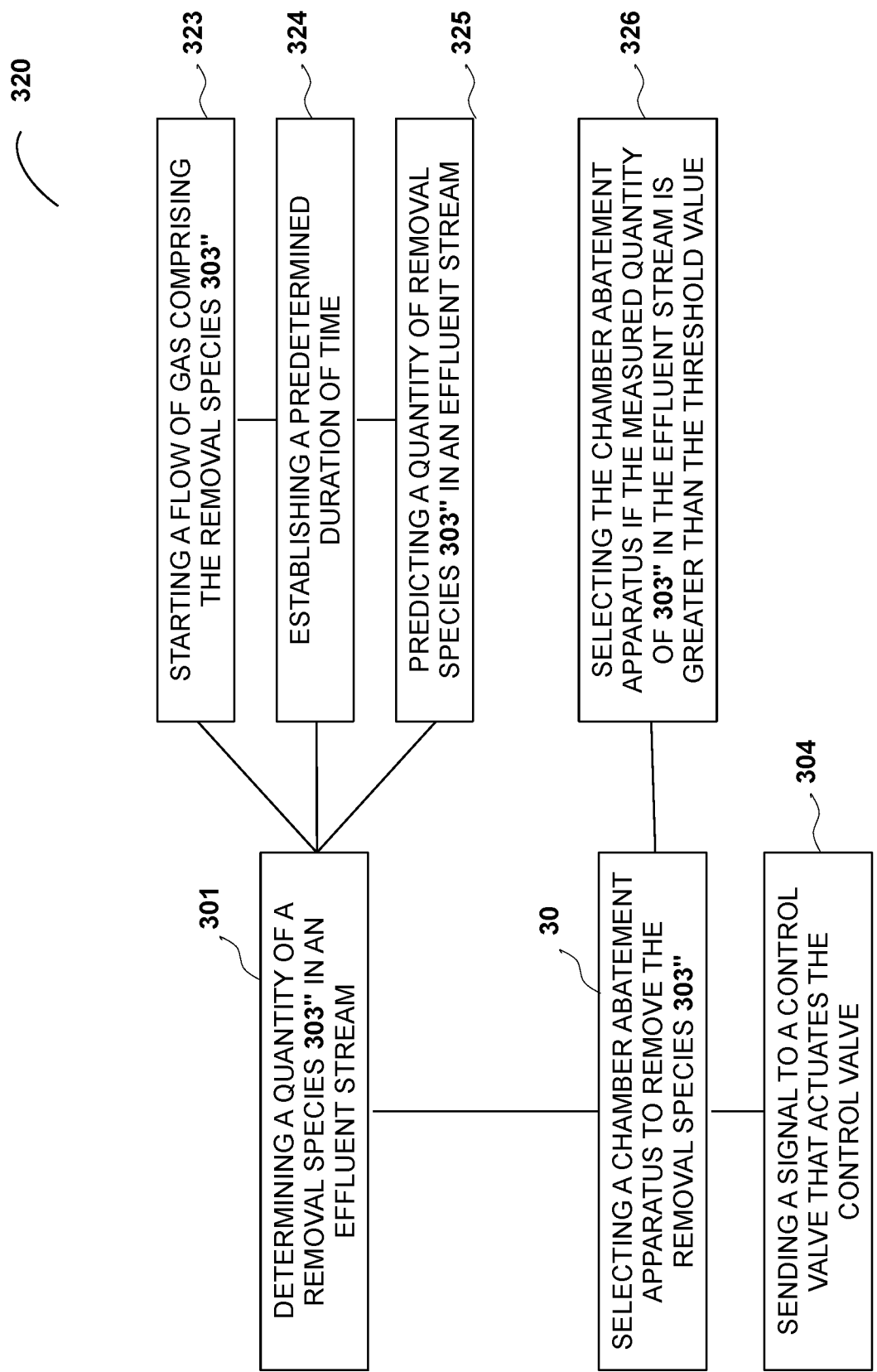
FIG. 3C depicts a computer system programmed to perform a method in accordance with some embodiments.

Referring to FIG. 3C, an embodiment of a computer system programmed to perform a method of selecting a chamber abatement apparatus is provided. The method 320 includes operations 301 and 302 of FIG. 3A/3B, and the removal species is 303". Determining a quantity of the removal species 303" in an effluent stream in the chamber exhaust flowing from the substrate processing chamber further includes starting a flow of gas containing the removal species 303" into the substrate processing chamber, at operation 323; establishing a predetermined duration of time at operation 324; and predicting a quantity of the removal species in an effluent stream in a chamber exhaust flowing from the semiconductor process chamber, at operation 325. In some embodiments, the predetermined duration of time at operation 324 is the time delay when the absorber can be bypassed if the quantity of the removal species is below a threshold value of the removal species.

Predicting a quantity of the removal species in an effluent stream in a chamber exhaust flowing from the substrate processing chamber at a given point in time may be based on one or more of a volumetric flow rate, Q ($m^3$/sec), of a gas comprising the removal species flowing from the substrate processing chamber; the duration of the time delay; a quantity of the removal species in a gas being introduced into the substrate processing chamber; a quantity of the removal species which reacts with (and/or etches) a wafer, chamber wall, and/or other component inside the substrate processing chamber (this indicates the quantity of removal species in the effluent stream in a chamber exhaust flowing from the substrate processing chamber); a cross-sectional area of an effluent stream pipe/tube that connects the substrate processing chamber and the chamber abatement apparatus; and a length of the effluent stream pipe/tube between the substrate processing chamber and the chamber abatement apparatus.

The embodiment of FIG. 3C further includes selecting a chamber abatement apparatus to remove the removal species 303", for example, if the measured quantity of the removal species in the effluent stream is greater than a threshold value at operation 326. Operation 326 is the same as operation 316 of FIG. 3B.

In an embodiment, a computer system performs the instructions of a non-transitory computer readable medium. The non-transitory computer readable medium can contain instructions to perform the methods described herein. Alternately, the instructions to perform the methods described herein may be added to the non-transitory computer readable medium. As described above, the computer system is connected to a control valve, a substrate process chamber, and to various sampling points or locations of the gases in the semiconductor fab. The computer system can select a control valve that directs the flow of the effluent stream in a chamber exhaust flowing from the substrate processing chamber to a chamber abatement apparatus, which can be accomplished by a controller sending a signal to a control valve to change the flow pattern of the effluent such that the effluent flows through the absorber (or when the removal species is below a threshold level, bypasses the absorber). Selecting the chamber abatement apparatus may also be accomplished by a controller sending a signal to a first control valve which actuates a second control valve. Actuating may be accomplished by a pneumatic or fluid circuit. The second control valve then directs the flow of the effluent stream to the chamber abatement apparatus. In some embodiments, the method includes forming an epitaxial layer on a substrate in the substrate processing chamber.

Figure 3D:
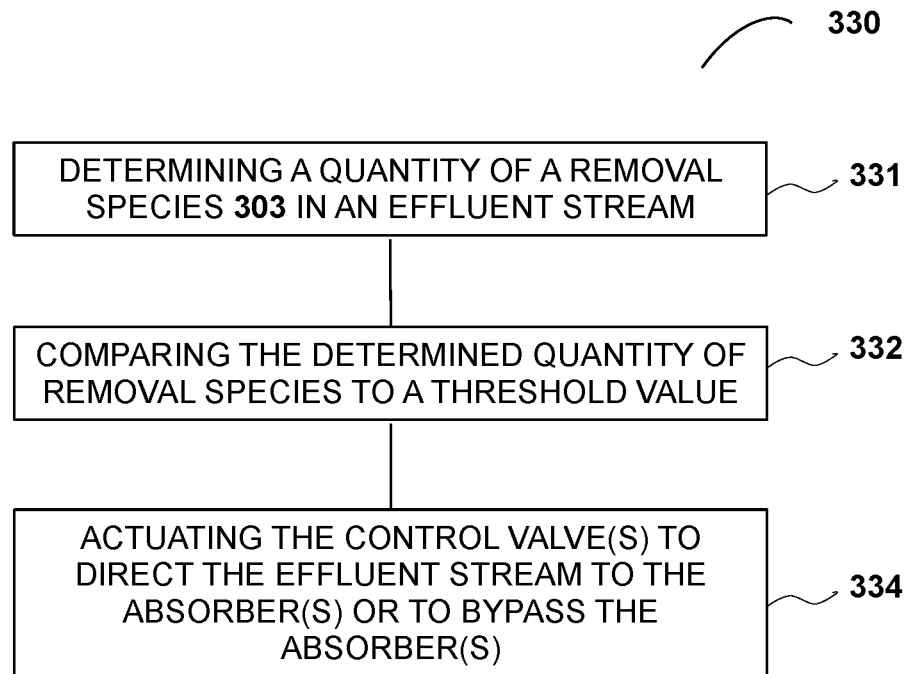
FIG. 3D depicts instructions of a non-transitory computer readable medium in accordance with some embodiments.

Referring to FIG. 3D, the instructions of the non-transitory computer readable medium cause a computer system to control a semiconductor manufacturing apparatus to perform a process. The process comprises determining a quantity of a removal species in an effluent stream in a chamber exhaust flowing from a substrate processing chamber, at operation 331; comparing the determined quantity of the removal species to a threshold value (i.e., a first threshold value of a first species and a second threshold value of a second species), at operation 332; and actuating one or more control valves to direct the effluent stream to an absorber or to direct the effluent stream to bypass the absorber, at operation 333. The first threshold value of a first species and second threshold value of a second species are threshold values of a species, including removal species and species that are not removal species. Based on the comparison, the computer system will select a control valve to change the flow path of the effluent stream in the chamber exhaust as described above. For example, if the determined quantity of the removal species is greater than the first threshold value of a first removal species, the control valve directs the effluent stream in the chamber exhaust to one or more absorbers. In contrast, if the determined quantity of the removal species is less than a second threshold value of second species, the control valve directs the effluent stream in the chamber exhaust to bypass the one or more absorbers. That is, the chamber abatement apparatus is selected for bypass mode (i.e., the absorber is bypassed) if the quantity is less than a second threshold value.

Determining a quantity of a removal species may further include one or more of operations 313-315 of FIG. 3B and operations 323-325 of FIG. 3C. Chemical analysis allows the quantity of the removal species to be resolved in the effluent stream in a chamber exhaust flowing from the substrate processing chamber, i.e., at operation 314 of FIG. 3B, and thereby also allows for resolving a difference between the predicted quantity of the removal species and the detected quantity of the removal species. Resolving this difference between the predicted quantity of the removal species and the detected quantity of the removal species may include setting the determined quantity of the removal species as the higher of the predicted quantity of the removal species and the detected quantity of the removal species.

The instructions to perform a process of bypassing an absorber may further comprise controlling the semiconductor fab to perform a manufacturing process on a semiconductor substrate, including substrate deposition processes, chamber clean processes, substrate etch processes as described in FIGS. 1A and 1B. Controlling the semiconductor fab may comprise providing a target flow rate to flow controllers in the substrate processing chamber. The target flow rate of materials may include, for example, the flow rates of a removal species during a deposition operation, a chamber clean operation, or an etch operation.

Figure 4:
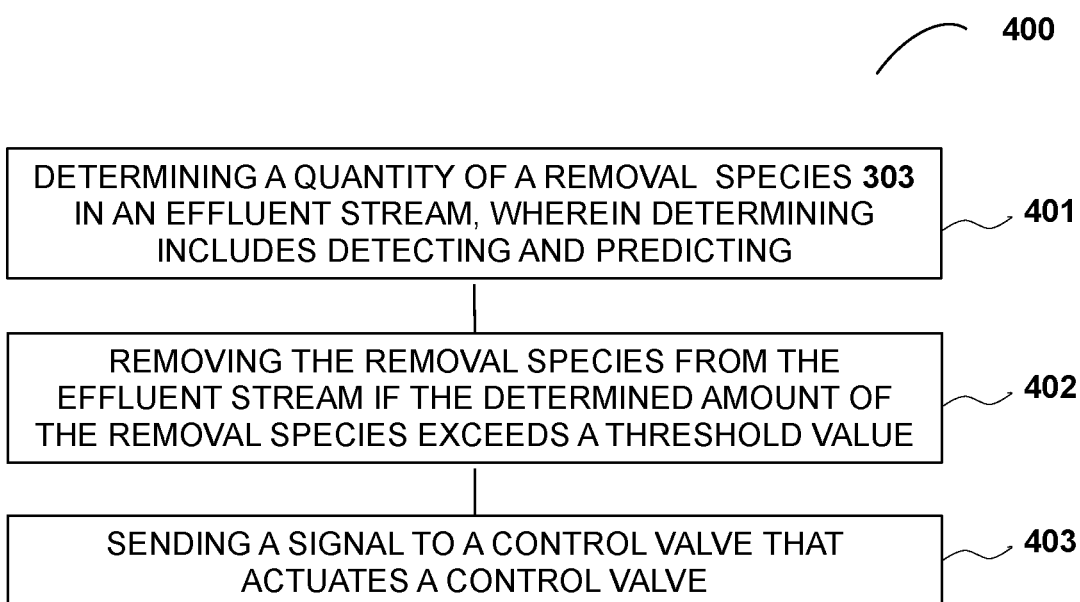
FIG. 4 is a flow diagram depicting a method of processing a substrate in accordance with some embodiments.

FIG. 4 is a flow diagram of a particular embodiment of a method 400 of processing a substrate. The method 400 includes determining a quantity of a removal species in an effluent stream in a chamber exhaust of a substrate processing chamber, wherein determining comprises detecting and predicting a quantity of the species, at operation 401. Operation 401 may include one or more of operations 313-315 of FIG. 3B and operations 323-325 of FIG. 3C. Determining a quantity of species in the effluent stream occurs upstream of the chamber abatement apparatus.

Method 400 further includes removing the removal species from the effluent stream of a chamber exhaust flowing from the substrate processing chamber if the determined quantity of the removal species exceeds a threshold value, at operation 402. For example, if the removal species in an effluent stream of the chamber exhaust is an arsenic containing material, the method will determine the quantity of arsine species in the effluent stream, and remove the arsine species from the effluent stream of the chamber exhaust using the absorber if the quantity of arsine species exceeds a threshold value of arsine species.

A threshold value of a removal species may be selected based upon variables such as operating parameters of the substrate processing chamber and the absorber. Because the threshold value is related to the time delay, the time delay may be selected based on sampling of the effluent stream in a chamber exhaust flowing from the substrate processing chamber at various stages of the semiconductor fab. Such sampling may be performed at detection points 210, 211, and 212 in FIG. 2. Alternatively, the threshold value may be the value specified by the semiconductor device manufacturing facility for an exhaust stream to enter the house exhaust, or may be a value specified by government or other regulation.

Removing the removal species from the effluent stream in a chamber exhaust flowing from the substrate processing chamber may, for example, include selecting a chamber abatement apparatus configured to remove the removal species. Such a process may include operating a valve that directs the flow of the effluent stream to the chamber abatement apparatus. This can be accomplished by a controller sending a signal to a control valve to change the flow path of the effluent stream in the chamber exhaust such that the effluent stream flows through the absorber, (or when the removal species is below a threshold level, bypasses the absorber), at operation 403. Selecting the chamber abatement apparatus may also be accomplished by a controller sending a signal to a control valve which actuates the control valve. Actuating may be accomplished by a pneumatic or fluid circuit. The control valve then directs the flow of the effluent stream in the chamber exhaust to the chamber abatement apparatus. In some embodiments, the method includes forming an epitaxial layer on a substrate in the substrate processing chamber.

Figure 5:
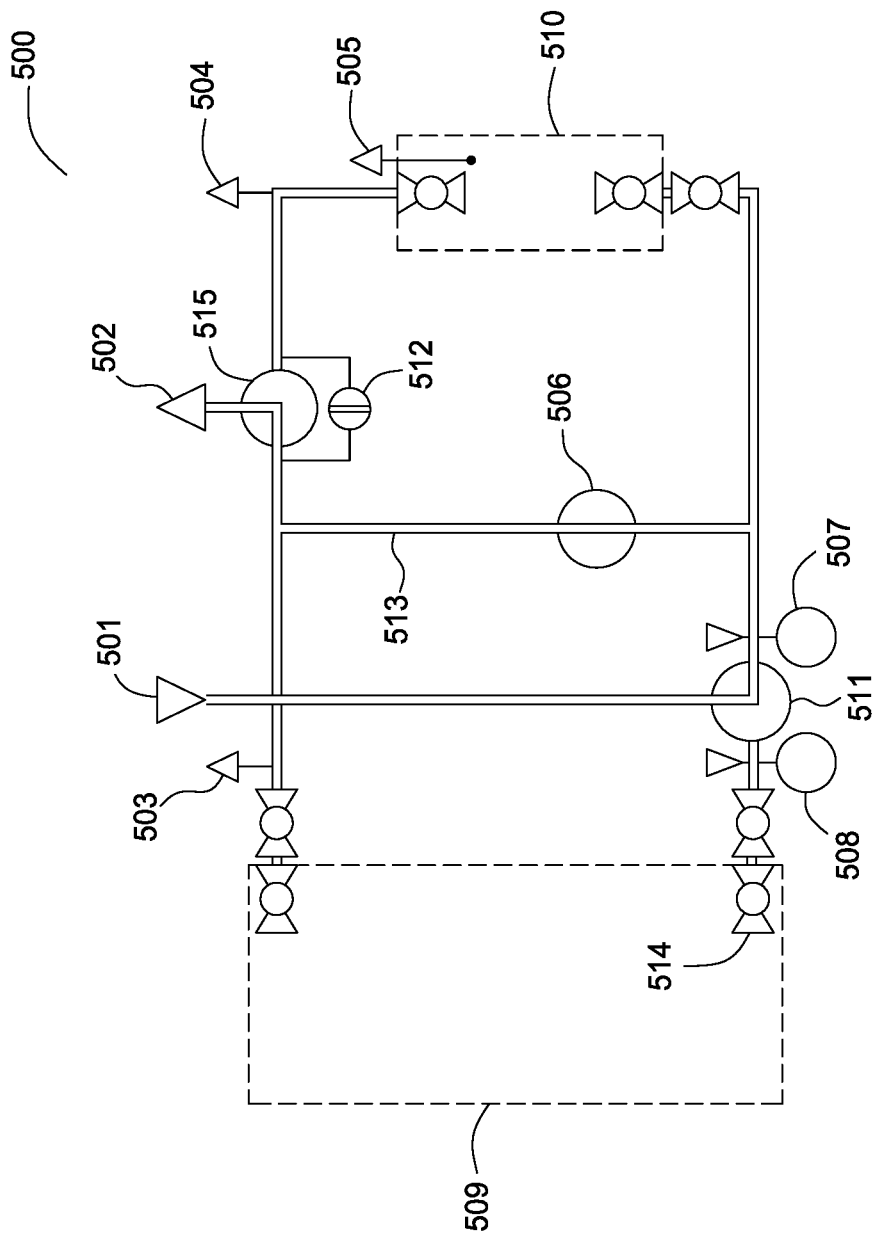
FIG. 5 depicts a chamber abatement apparatus in accordance with some embodiments.

FIG. 5 shows a chamber abatement apparatus, according to some embodiments. The chamber abatement apparatus includes a bypass, which allows bypass of an absorber. The bypass line 513 is connected through a series of valves to absorbers 509 and 510. Pressure indicators 507 and 508 indicate which absorber 509, 510 is in use by detecting the pressure of the effluent stream in the chamber exhaust flowing from the substrate processing chamber. Valves 506, 511, 512, 514, and 515 connect the lines through which effluent stream in a chamber exhaust of the substrate processing chamber flows. Absorbers may be connected in series or may be independent, or the absorbers can be bypassed. An effluent stream in a chamber exhaust of a substrate processing chamber (not shown) flows into the chamber abatement apparatus through inlet 501. Bypass line 513 connects the inlet 501 directly with the outlet 502 and is opened by means of a pneumatically actuated valve 506 while the connected lines are still able to vent to the house exhaust system if the manual valves are open. If a threshold value of a removal species in the effluent stream of the chamber exhaust is exceeded, the pneumatically actuated bypass valve 506 closes, and in turn, the bypass line 513 is closed. When the bypass line 513 is closed, the effluent stream flows to an abatement apparatus, such as absorber 509. The bypass mode can also be selected manually by an operator.

Detection points 503, 504, and 505 are located to allow sampling of the effluent stream at various stages of the chamber abatement apparatus. Detection point 503 allows detection of a removal species in an effluent stream of the chamber exhaust coming from the primary absorber 509. Chemical analysis may determine that there is a removal species in the effluent stream at or above the threshold value at the detection point 503 and the chamber abatement apparatus system can switch to a secondary absorber 510. In the secondary absorber 510, a detection point 505 represents a sampling port. Sampling at the detection point 505 may act as a secondary safety measure as its location may be about 90% up through the secondary absorber 510.

Sampling at detection points 503, 504, and 505 can allow an operator or a computer to feed-back data and information to the control system, for example to indicate a change in quantity of the removal species in the effluent stream of the chamber exhaust flowing from the substrate processing chamber. The controller of the control system will then take action. The action may be based on whether the determined quantity of the removal species exceeds a threshold value. For example, the controller may initially set the chamber abatement apparatus in a bypass mode. If the determined quantity of a removal species in the effluent stream of a chamber exhaust flowing from the substrate processing chamber is non-detectable or does not exceed a threshold value, the controller maintains the bypass mode. In contrast, if the controller determines, by either detecting (via a detector) or predicting that the determined quantity of the removal species (i.e., arsine compounds) exceeds a threshold value, the controller will control the process to switch the flow of the effluent stream to the absorber.

Additionally, the chamber abatement apparatus and methods herein allow for flexibility when not in the bypass mode. For example, in an embodiment, if a removal species is detected at the detection point 503 (after the effluent stream exits the primary absorber 509), the effluent stream containing the removal species would flow through the secondary absorber 510. Moreover, the chamber abatement apparatus and methods herein allow for concurrently predicting or detecting a quantity of a species in an effluent stream of the chamber exhaust flowing from a substrate processing chamber.

The descriptions of the various embodiments of the present disclosure have been presented for purposes of illustration, but are not intended to be exhaustive or limited to the embodiments disclosed. While the foregoing is directed to embodiments of the present disclosure, other and further embodiments of the disclosure may be devised without departing from the basic scope thereof, and the scope thereof is determined by the claims that follow. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system programmed to perform a method, comprising:
    an algorithm stored in a memory of the system, wherein the algorithm comprises a number of instructions which, when executed by a processor, causes a method to be performed comprising:
        determining a quantity of a removal species in an effluent stream flowing from a substrate processing chamber, wherein determining comprises:
            detecting or predicting a quantity of the removal species upstream of a chamber abatement apparatus in the effluent stream flowing from the substrate processing chamber; and
        selecting a chamber abatement apparatus to remove the removal species, wherein selecting is based on the quantity of the removal species reaching a threshold value.

2. The system of claim 1, wherein selecting comprises:
    operating a switch that directs the flow of the effluent stream to the chamber abatement apparatus.

3. The system of claim 1, wherein determining further comprises:
    starting a flow of a gas comprising the removal species to the substrate processing chamber; and then
    predicting the quantity of the removal species in the effluent stream flowing from the substrate processing chamber.

4. The system of claim 3, wherein predicting is based on:
    a time delay;
    a volumetric flow rate of a gas comprising the removal species flowing from the substrate processing chamber;
    a quantity of the removal species in a gas being introduced into the substrate processing chamber;
    a quantity of the removal species which reacts with or etches a wafer, chamber wall, or other component inside the substrate processing chamber;
    a cross-sectional area of an effluent stream pipe that connects the substrate processing chamber and the chamber abatement apparatus;

a length of the effluent stream pipe/tube between the substrate processing chamber and the chamber abatement apparatus; or combinations thereof.

5. The system of claim 3, wherein determining further comprises:
   detecting the removal species in the effluent stream flowing from the substrate processing chamber using chemical analysis;
   resolving a quantity of the removal species in the effluent stream; and
   comparing the quantity of the removal species in the effluent stream to a threshold value of the removal species.

6. The system of claim 5, wherein chemical analysis is performed by an optical method.

7. The system of claim 6, wherein chemical analysis is performed by gas chromatography (GC), Fourier transform infrared spectroscopy (FTIR), solid state gas detection, electrochemical gas detection, or color change of a reactive media.

8. The system of claim 1, wherein the removal species comprises an arsenic containing material, a phosphorus containing material, a cyanide containing material, or a phosgene.

9. The system of claim 1, further comprising forming an epitaxial structure.

\* \* \* \* \*

UNITED STATES PATENT AND TRADEMARK OFFICE
CERTIFICATE OF CORRECTION

PATENT NO. : 10,586,744 B2
APPLICATION NO. : 15/934679
DATED : March 10, 2020
INVENTOR(S) : David K. Carlson Page 1 of 1

It is certified that error appears in the above-identified patent and that said Letters Patent is hereby corrected as shown below:

In the Claims

In Column 14, Line 65, in Claim 4, delete "pipe" and insert -- pipe/tube --, therefor.

Signed and Sealed this
Twenty-sixth Day of May, 2020

Andrei Iancu
*Director of the United States Patent and Trademark Office*